United States Patent
Prandi

(10) Patent No.: US 8,137,351 B2
(45) Date of Patent: Mar. 20, 2012

(54) CLAMP FOR POSITIONING A SUPERELASTIC OSTEOSYNTHESIS CLIP

(75) Inventor: Bernard Prandi, Rennes (FR)

(73) Assignee: Memometal Technologies (FR)

(*) Notice: Subject to any disclaimer, the term of this patent is extended or adjusted under 35 U.S.C. 154(b) by 795 days.

(21) Appl. No.: 10/599,962

(22) PCT Filed: Apr. 15, 2005

(86) PCT No.: PCT/FR2005/050245
§ 371 (c)(1),
(2), (4) Date: Sep. 30, 2008

(87) PCT Pub. No.: WO2005/104961
PCT Pub. Date: Nov. 10, 2005

(65) Prior Publication Data
US 2009/0018556 A1    Jan. 15, 2009

(30) Foreign Application Priority Data

Apr. 16, 2004  (FR) ...................................... 04 04235

(51) Int. Cl.
*A61B 17/56* (2006.01)
(52) U.S. Cl. ....................................................... 606/75
(58) Field of Classification Search ............... 606/75, 606/210, 151, 142, 205–208, 211; 81/315, 81/300, 313–314, 318, 321, 324–325, 328, 81/336–338; 433/3–4, 159–160
See application file for complete search history.

(56) References Cited

U.S. PATENT DOCUMENTS

| | | | | |
|---|---|---|---|---|
| 2,222,744 A * | 11/1940 | Gallien, Jr. | ...................... | 72/392 |
| 3,041,712 A * | 7/1962 | Wurzel | ........................... | 29/229 |
| 3,926,195 A | 12/1975 | Bleier et al. | ................... | 128/346 |
| 4,462,404 A | 7/1984 | Schwarz et al. | ............... | 128/321 |
| 5,141,514 A * | 8/1992 | van Amelsfort | ............... | 606/117 |
| 6,261,296 B1 * | 7/2001 | Aebi et al. | ....................... | 606/90 |
| 6,635,072 B1 * | 10/2003 | Ramamurti et al. | .......... | 606/208 |
| 6,685,708 B2 | 2/2004 | Monassevitch et al. | ........ | 606/75 |
| 7,189,234 B2 * | 3/2007 | Zucherman et al. | ........... | 606/249 |
| 2002/0072752 A1* | 6/2002 | Zucherman et al. | ............ | 606/99 |

FOREIGN PATENT DOCUMENTS

| | | |
|---|---|---|
| DE | 3337447 | 5/1985 |
| DE | 19725597 | 10/1998 |
| FR | 1080876 | 12/1954 |

* cited by examiner

*Primary Examiner* — Melanie Tyson
*Assistant Examiner* — Son Dang
(74) *Attorney, Agent, or Firm* — Lerner, David, Littenberg, Krumholz & Mentlik, LLP

(57) ABSTRACT

A clamp has two arms with gripping jaws for supporting and positioning a superelastic osteosynthesis clip, The osteosynthesis clip comprising a web from which two flanges to be inserted into two portions of bone emerge. The clamp also has a component for preventing the jaws from being opened beyond a point at which the angle between the flanges of a clamp supported clip is greater than 90°; and a second component for preventing the jaws from being closed beyond a point at which the angle between the flanges and the web is substantially 90°.

9 Claims, 4 Drawing Sheets

US 8,137,351 B2

CLAMP FOR POSITIONING A SUPERELASTIC OSTEOSYNTHESIS CLIP

CROSS REFERENCE TO RELATED APPLICATIONS

This is a Section 371 filing of international application No. PCT/FR2005/050245 filed Apr. 15, 2005, and published, in French, as International Publication No. WO 2005/104961 A1 on Nov. 10, 2005, and claims priority of French Application No. 0404235 filed on Apr. 16, 2004, which applications are hereby incorporated by reference herein, in their entirety.

FIELD OF THE INVENTION

The invention relates to the field of surgical tools used to treat patients suffering from fracture or fissure fracture type lesions or who have undergone corrective surgical osteotomy requiring osteosynthesis. The invention makes it possible to fit an element that is used to keep two portions of bone in position, thereby encouraging bone regrowth between these two portions.

The invention relates more especially to a clamp that is used to hold a clip before it is used and inserted into the two portions of bone and that are to be knitted back together.

DESCRIPTION OF THE PRIOR ART

Those who are skilled in the art are perfectly familiar with the use of shape-memory clips that allow compression of the pieces of bone to be joined together in order to carry out this type of osteosynthesis.

A distinction is generally made between cold clips that need to be placed in a freezer and resume their shape (at approximately 37° C.) and clips that have to be heated rather than chilled before they are fitted.

It is also known that the compression force of the clip depends on the temperature at which it resumes its shape. The compression force of a cold clip exceeds that of a hot clip and this force varies within a single clip product line due to industrial manufacturing temperature tolerances.

Those skilled in the art are also familiar with so-called superelastic clips that are made of a shape-memory alloy obtained when martensite is created by deformation of their initial austenitic structure. U.S. Pat. No. 4,665,906 discloses the characteristic curve of this type of superelastic clip. This type of clip therefore has the advantage that it does not have to be cooled or heated before impacting.

Given the characteristics of these superelastic clips, especially in terms of their compression force, they can be awkward to fit.

Generally speaking, clamps designed to hold the parallel flanges of the clip apart, i.e. in the position in which they are surgically inserted, are used to fit superelastic type osteosynthesis clips. When not pulled apart, the flanges of the clip are close to each other. When the clip is placed inside the gripping tips of the clamps, the two flanges are spread apart parallel to each other in order to produce, between said flanges, a compression force after impacting in the bone.

However, using these systems, it is not possible to provide a constant force if deformation of the clip varies over time. In fact, when the two flanges are spread apart, immediately after the clip is inserted, a relatively high compression force is exerted between the two flanges of the clip. As soon as the clip has a certain amount of clearance relative to the recesses in which it is impacted, the compression force between the two flanges then drops substantially by half.

The invention has set itself the object of overcoming these drawbacks in a simple, dependable, effective and efficient manner.

SUMMARY OF THE INVENTION

The problem that the invention intends to solve is to provide a means making it possible to impact a superelastic clip by generating a known, virtually constant pressure between its flanges once it has been impacted between the two portions of bone that are to be knitted back together.

In order to solve such a problem, a clamp comprising, in a known manner, two arms with gripping tips in the form of two jaws for supporting and positioning a superelastic osteosynthesis clip has been designed and developed. This type of osteosynthesis clip has a web or base from which two flanges intended to be inserted into the two portions of bone emerge.

According to the invention, this clamp is characterized in that it comprises:

a first means for preventing the jaws of each arm from being opened in order to prevent the clip from opening beyond a point at which the angle between the flanges and the web is greater than 90°;

a second means for preventing the jaws from being closed in order to prevent the clip from closing beyond a point at which the angle between the flanges and the web is substantially 90°;

In other words, when a clip is placed between the jaws of the clamp, pressure exerted by the surgeon on the two arms of the clamp makes it possible to straighten the flanges of the clip into an "over-opened" position. In this case, the first means is used as a limit stop for opening of the jaws of the clamp when over-opening of the flanges is sufficient.

In fact, provision can be made for this limit stop to be adjustable by the surgeon depending, in particular, on the type of clip.

The second means is also capable of acting as a limit stop when the surgeon releases the arms of the clamp once the flanges of the clip are over-opened. This second means then makes it possible to position the flanges of the clip parallel to each other, i.e. at 90°, relative to the web of the clip. This arrangement then makes it possible to impact the clip in the two portions of bone that are to be knitted back together.

Advantageously, the first means may comprise a component that is separately mounted on one of the arms. In other words, in a first version, the first limit stop can be obtained by means of an ancillary component separately mounted on one of the arms.

In a second version, the first means may comprise a protuberance on one of the arms. In other words, the limit stop used to stop opening of the jaws is obtained by means of a protuberance on one of the arms.

In practice, the first means may come into contact with the opposite arm in order to make it possible to prevent opening of the jaws.

In other words, regardless of the form of limit stop used for the first means, opening of the jaws is prevented by the fact that the first means comes into contact with the opposite arm of the clamp.

Advantageously, the second means may comprise a component separately mounted on one of the arms and comprising at least one tooth that cooperates with a sharp edge on the opposite arm.

In other words, one of the arms of the clamp comprises a separately mounted component that also cooperates with the other arm. As the jaws are opening, this separately mounted component slides freely on the opposite arm. However, once the jaws are opened to their maximum extent, the jaws close again until at least one tooth of the separately mounted component comes up against the sharp edge on the opposite arm.

Advantageously the separately mounted component may swivel relative to the arm on which it is mounted. In other words, the separately mounted component providing the second limit stop is swivelably connected relative to one of the arms.

In practice, both the arms may comprise an elastic return means making it possible to keep them apart. In other words, when the surgeon releases pressure on the arms, opening of the arms is then automatically produced by the elastic return means.

In certain cases, the first means may be adjustable so as to allow variation in the extent of over-opening of the clip. Thus, depending on the type of clip used, the surgeon can modify the maximum over-opening angle of the flanges of the clip relative to its web. This can make it possible to impact various type of clips using the same clamp.

Similarly, the second means may be adjustable so as to allow parallel positioning of the flanges of the clip depending on the size of its web. In fact, if the size of the web of the clip varies depending on the type of lesion to be treated, it may be necessary to adapt the second limit stop.

BRIEF DESCRIPTION OF THE DRAWINGS

In order that the way in which the invention is implemented and its resulting advantages may more readily be understood, the following description of an embodiment is given, merely by way of example, reference being made to the accompanying drawings.

DESCRIPTION OF THE PREFERRED EMBODIMENTS

As already stated, the invention relates to a clamp (1) making it possible to over-open a superelastic osteosynthesis clip (2).

Figure 2:
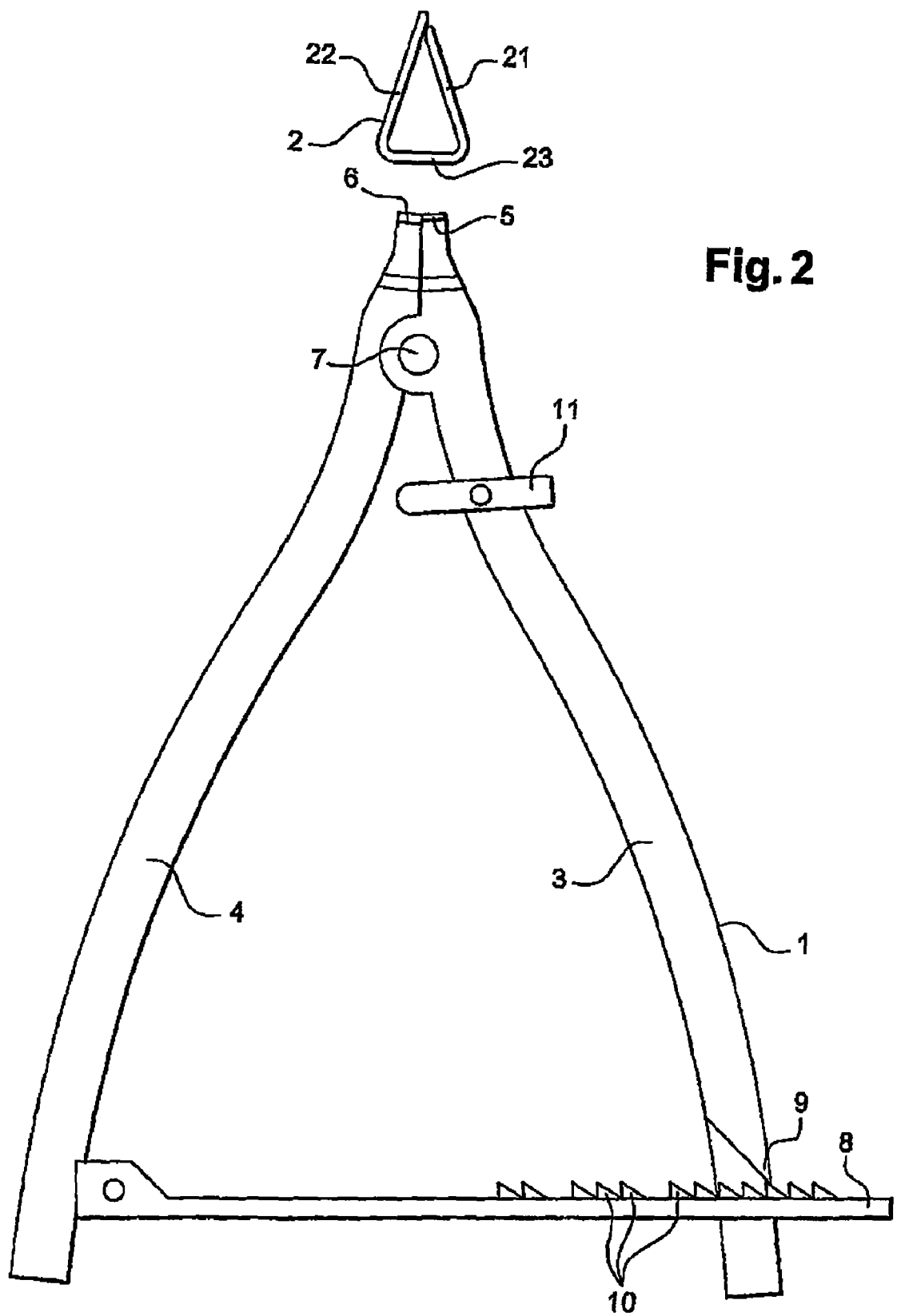
FIGS. 2 to 4 show front views of the clamp making it possible to illustrate the various stages of its use in accordance with the invention.

As shown in FIG. 2, the clamp (1) comprises two arms (3, 4) with gripping tips in the form of two jaws (5, 6). These two arms are connected and capable of swiveling around shaft (7). The actual clip (2) comprises a web (23) from which two flanges (21, 22) that are bent towards the inside of the clip when the clip is not in use emerge.

Figure 3:
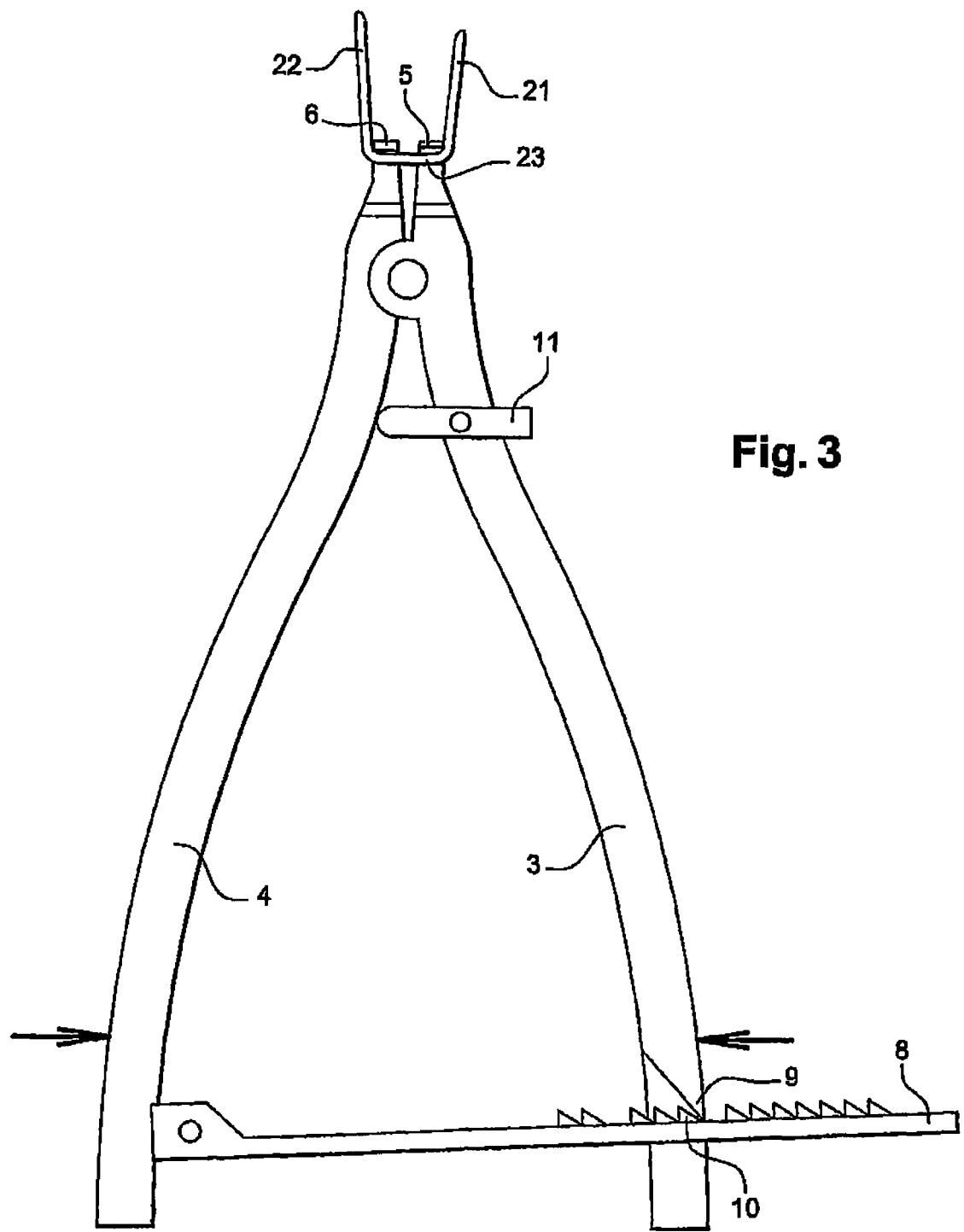

As shown in FIG. 3, when the surgeon exerts pressure on arms (3, 4) of clamp (1), jaws (5, 6) that are used to hold clip (2) then deform it. In fact, flanges (21, 22) are spread apart towards the outside of clip (2) so that they are in an over-opened position. In other words, the flanges (21, 22) of clip (2) form an angle relative to web (23) that exceeds 90°.

When sufficient deformation has been obtained, a component (11) that is physically attached or separately mounted on arm (3) comes into contact with the opposite arm (4). In this case, the surgeon cannot open clip (2) any further. The surgeon then releases the pressure on arms (3, 4) of clamp (1) and an elastic return means makes it possible to close the flanges (21, 22) of the clip back towards each other.

In a first version, this return means can be obtained by the actual elasticity of clip (2).

In another version, an elastic return means can be separately mounted on clamp (1).

Figure 4:
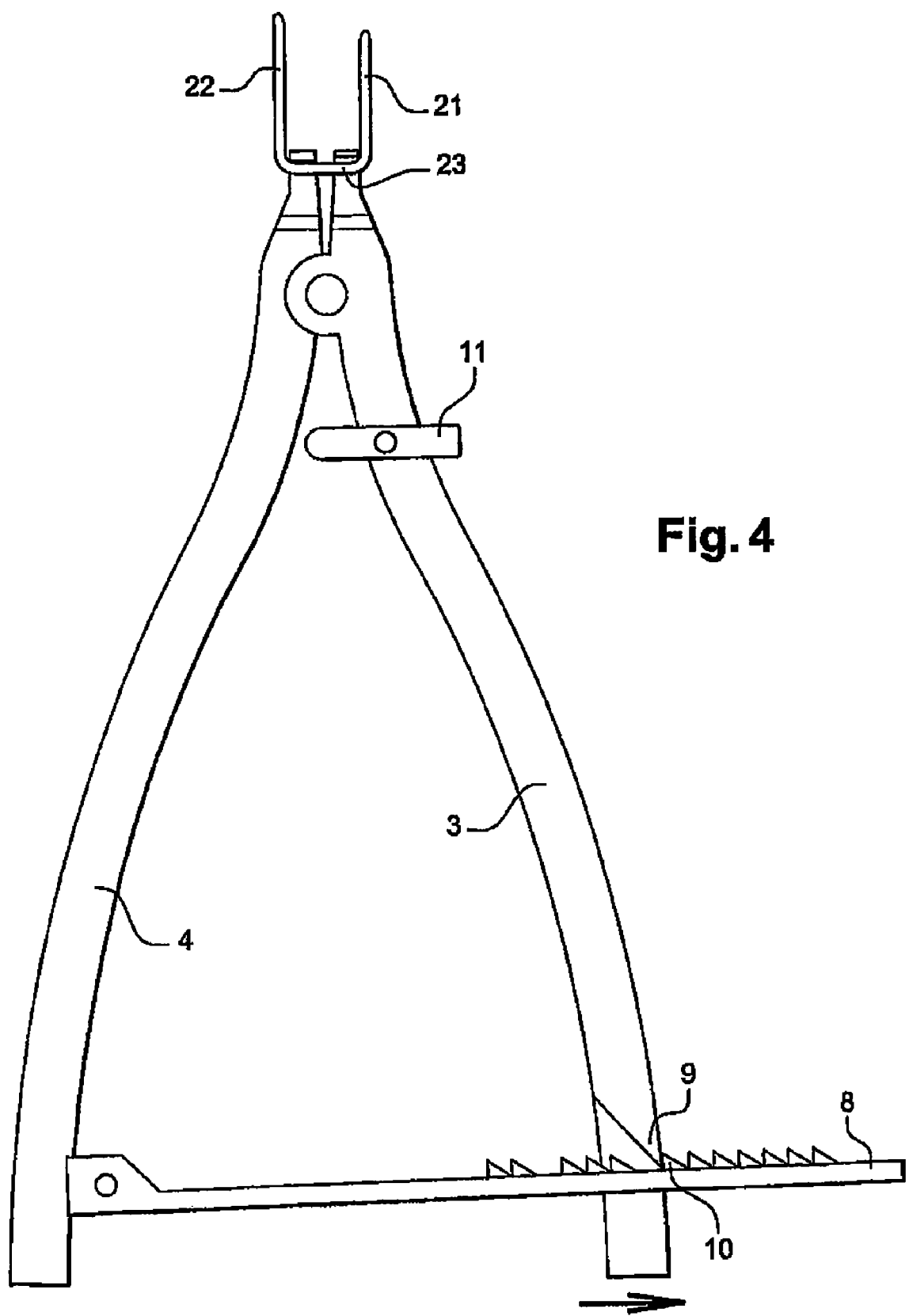

As shown in FIG. 4, when the pressure exerted on the arms of the clamp is released due to the effect of the return force, the second means then makes it possible to prevent closing of jaws (5, 6) so that flanges (21, 22) of clip (2) are parallel in order to be impacted inside the two portions of bone to be repaired.

This second means comprises at least one tooth (10) attached to a separately mounted component (8) swivelably connected relative to arm (4) of clamp (1). It also comprises a sharp edge (9) that is part of arm (3).

When tooth (10) is in contact with sharp edge (9), the clamp can no longer be opened and the surgeon can then impact clip with its flanges parallel but prevented from over-opening so as to perfectly control changes in the force it exerts over time once the clip has been impacted.

It should be noted that second means (9, 10) may be adjustable so as to allow parallel positioning of flanges (21, 22) of the clip depending on the dimensions of its web (23). For example, the separately mounted component may comprise several teeth and act as a rack.

The position of component (11) may also be adjustable in order to allow variation of the extent to which the clip is over-opened.

Figure 1:
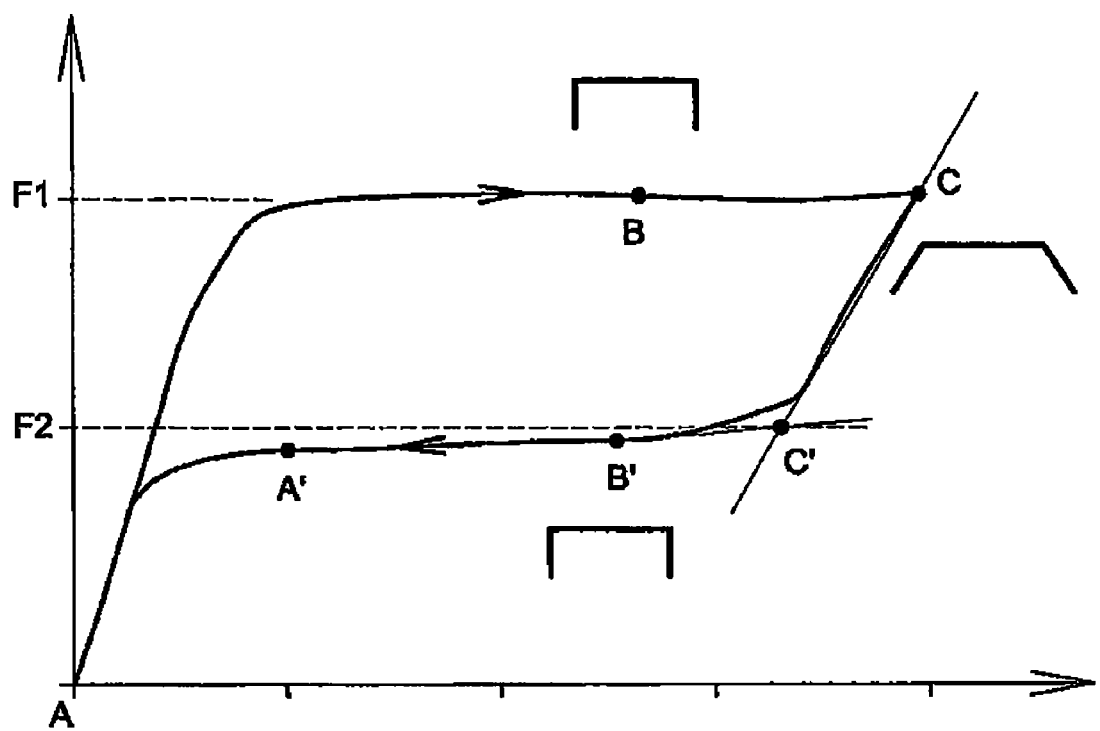
FIG. 1 shows the characteristic curve of the force exerted by a superelastic clip as a function of its deformation obtained by means of the clamp in accordance with the invention; part B/C represents opening of the clip and part C/B'/A' represents closing of the clip.

As shown in the graph in FIG. 1, at point A the clip is not in use and its flanges are bent inwards in the direction of its web. When arms (3) and (4) of the clamp are pressed, flanges (21, 22) straighten due to the effect of the jaws. The internal stress of the clip is then at level F1 at point B.

When first means (11) prevents opening of the jaws of the clamp, clip (2) is at point C thanks to the action on the first means of the clamp which enables over-opening of the clip. The surgeon then releases pressure on the arms of the clamp and the clip returns to its normal position for impacting, i.e. with its flanges parallel, at point B' in the graph. The stress is then F2 and remains stable if there should ever be any play. Arms (3) and (4) of the clamp are locked in position by second means (9, 10).

In the case of a superelastic osteosynthesis clip which has a deformation curve as a function of stress having a line B-C that represents opening of said clip and a line C-B'-A' that represents its closing, over-opening of said clip by first means (11) corresponds substantially to portion C-C' of the curve where C' corresponds to intersection of the tangent lines between the return plateau, closure B'-A' and the fall from C.

The above description makes it apparent that the clamp in accordance with the invention has many advantages, in particular:

it makes it possible to produce a surgical tool capable of guaranteeing stability of the compression provided by an osteosynthesis clip over time, thereby encouraging healing of the bony lesion and, especially, preventing any excess C/B' force;

it can be adapted to suit several clips having different dimensions or made of different materials;

The invention claimed is:

1. A clamp comprising two arms pivotally connected to each other, the arms having opposed gripping jaws supporting and positioning a superelastic osteosynthesis clip, said osteosynthesis clip comprising a web from which two flanges adapted to be inserted into two portions of bone emerge, said clamp further comprising:

a first means for preventing the jaws when supporting the clip from over-opening the clip beyond a limited extent at which an angle between the flanges and the web is greater than 90°; and a second means for preventing the jaws from being closed beyond a point at which the angle between the flanges and the web is substantially 90°.

2. The clamp as claimed in claim 1, wherein the first means comprises a component separately mounted on one of the arms.

3. The clamp as claimed in claim 1, wherein the first means comprises a protuberance on one of the arms.

4. The clamp as claimed in claim 3, wherein the first means comes into contact with an opposite arm of said two arms in order to prevent said opening of the jaws.

5. The clamp as claimed in claim 1, wherein the second means comprises a component separately mounted on one of the arms and comprising at least one tooth that cooperates with a sharp edge on an opposite arm of the two arms.

6. The clamp as claimed in claim 5, wherein the component can swivel relative to the arm on which the component is mounted.

7. The clamp as claimed in claim 1, wherein the first means is adjustable so as to allow variation in an extent of over-opening of the clip.

8. The clamp as claimed in claim 1, wherein the second means is adjustable so as to allow parallel positioning of the flanges of the clip depending on size of the web.

9. The clamp as claimed in claim 1, wherein, for a super-elastic osteosynthesis clip which has a deformation curve as a function of stress having a line B-C that represents opening of said clip and a line C-B'-A' that represents clip closing, over-opening of said clip by the first means corresponds substantially to portion C-C' of the curve where C' corresponds to intersection of tangent lines between a return plateau, closure B'-A' and a fall from C.

* * * * *